US010872499B1

(12) United States Patent
Russ et al.

(10) Patent No.: US 10,872,499 B1
(45) Date of Patent: Dec. 22, 2020

(54) ELECTRONIC GAMING MACHINES WITH PRESSURE SENSITIVE INPUTS FOR EVALUATING PLAYER EMOTIONAL STATES

(71) Applicant: IGT, Las Vegas, NV (US)

(72) Inventors: Michael Russ, Graz (AT); David Froy, Lakeville-Westmorland (CA); David Small, Moncton (CA); Stefan Keilwert, St. Josef (AT); Fayez Idris, Dieppe (CA)

(73) Assignee: IGT, Las Vegas, NV (US)

( * ) Notice: Subject to any disclaimer, the term of this patent is extended or adjusted under 35 U.S.C. 154(b) by 0 days.

(21) Appl. No.: 16/568,982

(22) Filed: Sep. 12, 2019

(51) Int. Cl.
*G07F 17/32* (2006.01)
*G06F 3/01* (2006.01)
*A63F 13/58* (2014.01)
*A63F 13/212* (2014.01)
*A61B 5/00* (2006.01)
*A61B 5/16* (2006.01)

(52) U.S. Cl.
CPC ............ *G07F 17/326* (2013.01); *A61B 5/165* (2013.01); *A61B 5/7271* (2013.01); *A63F 13/212* (2014.09); *A63F 13/58* (2014.09); *G06F 3/011* (2013.01); *G07F 17/3209* (2013.01); *G07F 17/3227* (2013.01); *G07F 17/3239* (2013.01); *G07F 17/3244* (2013.01); *G07F 17/3262* (2013.01); *G07F 17/3295* (2013.01); *A63F 2250/26* (2013.01); *A63F 2300/6045* (2013.01)

(58) Field of Classification Search
None
See application file for complete search history.

(56) References Cited

U.S. PATENT DOCUMENTS

| 8,241,912 | B2 | 8/2012 | Loose |
| 8,926,421 | B2 | 1/2015 | Arezina et al. |
| 8,956,224 | B2 | 2/2015 | Gagner et al. |
| 9,005,001 | B2 | 4/2015 | Jones et al. |
| 9,235,267 | B2 | 1/2016 | Burrough et al. |
| 9,384,626 | B2 | 7/2016 | Walker et al. |
| 10,180,723 | B2 | 1/2019 | Lisseman et al. |
| 2009/0143141 | A1 | 6/2009 | Wells et al. |
| 2009/0270170 | A1* | 10/2009 | Patton ................. G07F 17/3206 463/36 |
| 2012/0169610 | A1* | 7/2012 | Berkes ................. G06F 3/0414 345/173 |

(Continued)

FOREIGN PATENT DOCUMENTS

CN 103210429 10/2016

*Primary Examiner* — Jason T Yen
(74) *Attorney, Agent, or Firm* — Sage Patent Group

(57) ABSTRACT

Systems, devices and methods are provided. A system comprises a processor circuit and a memory coupled to the processor circuit. The memory comprises machine-readable instructions that, when executed by the processor circuit, cause the processor circuit to receive, from a pressure sensor of an input device of a gaming device, a first pressure parameter value corresponding to a first amount of pressure being applied by a player to the input device at a first input location for a first time duration, determine, based on the first amount of pressure and the first time duration, an emotional of the player. The processor circuit further modifies an operating characteristic of the gaming device based on the emotional state of the player.

20 Claims, 13 Drawing Sheets

(56) References Cited

U.S. PATENT DOCUMENTS

2013/0216126 A1\* 8/2013 Chen ...................... G06K 9/62
  382/156
2016/0144278 A1\* 5/2016 el Kaliouby ......... A61B 5/7271
  463/36
2019/0355209 A1\* 11/2019 Sorey ................. G07F 17/3213

\* cited by examiner

US 10,872,499 B1

ELECTRONIC GAMING MACHINES WITH PRESSURE SENSITIVE INPUTS FOR EVALUATING PLAYER EMOTIONAL STATES

BACKGROUND

Embodiments described herein relate to providing input for gaming devices, and in particular to pressure inputs for gaming devices, and related devices, systems, and methods.

Gaming devices, such as electronic gaming machines (gaming devices), may provide input devices for facilitating play of a game by a player at the gaming device, and for providing additional interactive functionality at the gaming device. Many conventional gaming devices employ relatively simple input devices, such as buttons or keypads, which limit the features and functionality that can be offered at the gaming device.

BRIEF SUMMARY

Some embodiments herein are directed to a gaming device that includes an input device that includes multiple input locations and a pressure sensor to detect, for each input location, an amount of pressure applied by a player to the input device at the input location of the gaming device. The gaming device further includes a processor circuit and a memory coupled to the processor circuit. The memory includes machine-readable instructions that, when executed by the processor circuit, cause the processor circuit to perform operations including receiving, from the pressure sensor, a first pressure parameter value corresponding to a first amount of pressure being applied by the player to the input device at a first input location for a first time interval comprising a first time duration, determining, based on the first amount of pressure, an emotional state of the player and modifying an operation of the gaming device based on the emotional state of the player.

Some embodiments herein are directed to a system that includes a processor circuit and a memory coupled to the processor circuit. The memory includes machine-readable instructions that, when executed by the processor circuit, cause the processor circuit to receive, from a pressure sensor of an input device of a gaming device, a first pressure parameter value corresponding to a first amount of pressure being applied by a player to the input device at a first input location for a first time duration. The processor circuit is further caused to determine, based on the first amount of pressure and the first time duration, an emotional state of the player and to modify an operating characteristic of the gaming device based on the emotional state of the player.

Some embodiments are directed to methods that include operations of detecting, by a pressure sensor of an input device of a gaming device, an amount of pressure applied by a player to the input device that includes multiple input locations. Operations include detecting, by the pressure sensor, a time duration of the pressure applied to the input device, receiving, into a processor circuit of the gaming device, a first pressure parameter value corresponding to the amount of pressure being applied to the input device at a first one of the locations, comparing the first pressure parameter value to a high pressure parameter threshold and to a low pressure parameter threshold that is lower than the high pressure parameter threshold, and responsive to the first pressure parameter value being greater than the high pressure parameter threshold, modifying the game play to increase a speed of game play. Operations further include, responsive to the first pressure parameter value being less than the low pressure parameter threshold, modifying the game play to decrease a speed of game play.

DETAILED DESCRIPTION

Figure 1:
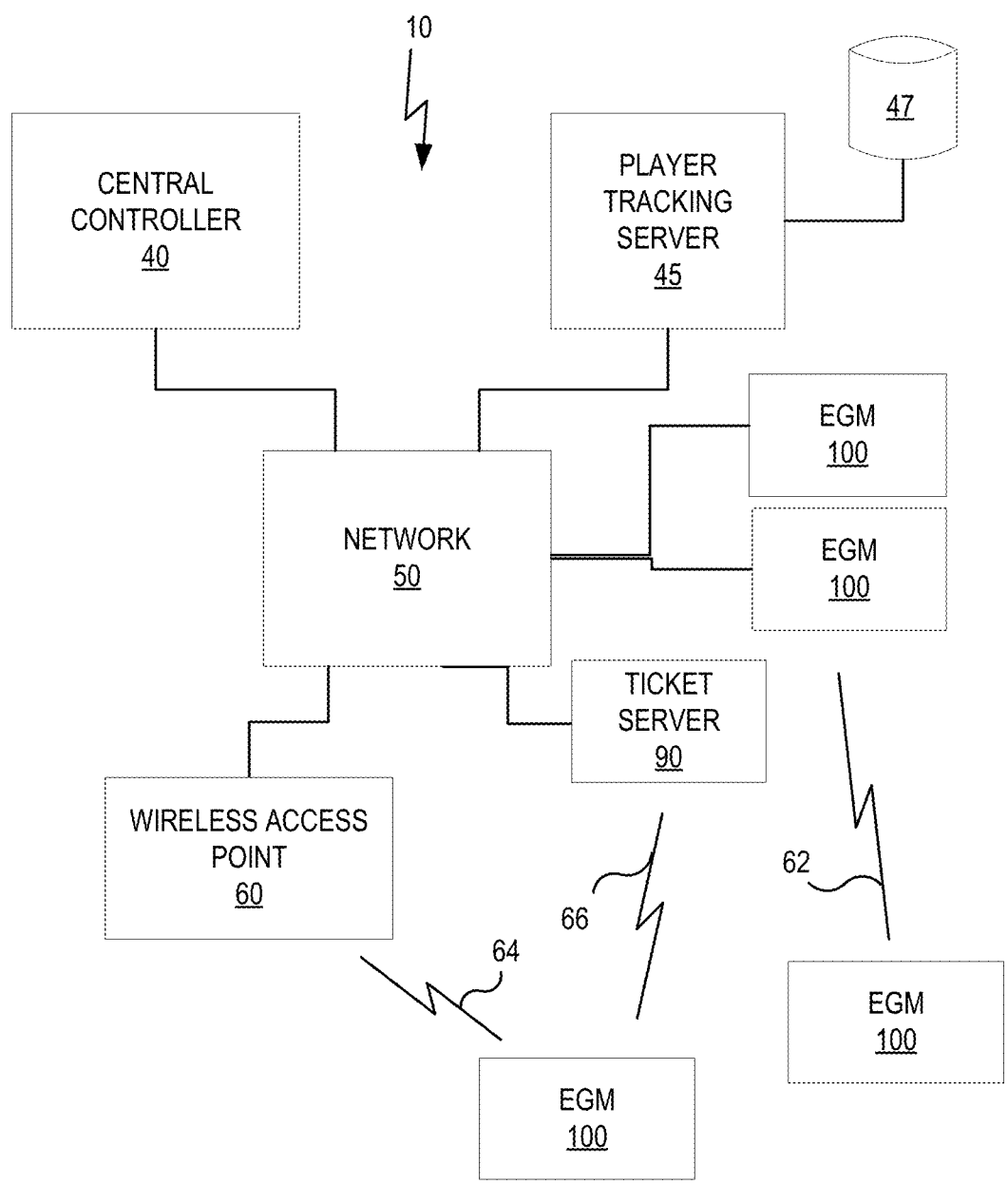
FIG. 1 is a schematic block diagram illustrating a network configuration for a plurality of gaming devices according to some embodiments.

Referring to FIG. 1, a gaming system 10 including a plurality of gaming devices 100 is illustrated. As discussed above, the gaming devices 100 may be one type of a variety of different types of gaming devices, such as electronic gaming machines (EGMs), mobile devices, or other devices, for example. The gaming system 10 may be located, for example, on the premises of a gaming establishment, such as a casino. The gaming devices 100, which are typically situated on a casino floor, may be in communication with each other and/or at least one central controller 40 through a data communication network 50 that may include a remote communication link. The data communication network 50 may be a private data communication network that is operated, for example, by the gaming facility that operates the gaming devices 100. Communications over the data communication network 50 may be encrypted for security. The central controller 40 may be any suitable server or computing device which includes at least one processing circuit and at least one memory or storage device. Each gaming device 100 may include a processing circuit that transmits and receives events, messages, commands or any other suitable data or signal between the gaming device 100 and the central controller 40. The gaming device processing circuit is operable to execute such communicated events, messages or commands in conjunction with the operation of the gaming device 100. Moreover, the processing circuit of the central controller 40 is configured to transmit and receive events, messages, commands or any other suitable data or signal between the central controller 40 and each of the individual gaming devices 100. In some embodiments, one or more of the functions of the central controller 40 may be performed by one or more gaming device processing circuits. Moreover, in some embodiments, one or more of the functions of one or more gaming device processing circuits as disclosed herein may be performed by the central controller 40.

A wireless access point 60 provides wireless access to the data communication network 50. The wireless access point 60 may be connected to the data communication network 50 as illustrated in FIG. 1, and/or may be connected directly to the central controller 40 or another server connected to the data communication network 50.

A player tracking server 45 may also be connected through the data communication network 50. The player tracking server 45 may manage a player tracking account that tracks the player's gameplay and spending and/or other player preferences and customizations, manages loyalty awards for the player, manages funds deposited or advanced on behalf of the player, and other functions. Player information managed by the player tracking server 45 may be stored in a player information database 47.

As further illustrated in FIG. 1, the gaming system 10 may include a ticket server 90 that is configured to print and/or dispense wagering tickets. The ticket server 90 may be in communication with the central controller 40 through the data network 50. Each ticket server 90 may include a processing circuit that transmits and receives events, messages, commands or any other suitable data or signal between the ticket server 90 and the central controller 40. The ticket server 90 processing circuit may be operable to execute such communicated events, messages or commands in conjunction with the operation of the ticket server 90. Moreover, in some embodiments, one or more of the functions of one or more ticket server 90 processing circuits as disclosed herein may be performed by the central controller 40.

The gaming devices 100 communicate with one or more elements of the system 10 to coordinate providing wagering games and other functionality. For example, in some embodiments, the gaming device 100 may communicate directly with the ticket server 90 over a wireless interface 62, which may be a WiFi link, a Bluetooth link, an NFC link, etc. In other embodiments, the gaming device 100 may communicate with the data communication network 50 (and devices connected thereto, including other gaming devices 100) over a wireless interface 64 with the wireless access point 60. The wireless interface 64 may include a WiFi link, a Bluetooth link, an NFC link, etc. In still further embodiments, the gaming devices 100 may communicate simultaneously with both the ticket server 90 over the wireless interface 66 and the wireless access point 60 over the wireless interface 64. Some embodiments provide that gaming devices 100 may communicate with other gaming devices over a wireless interface 64. In these embodiments, wireless interface 62, wireless interface 64 and wireless interface 66 may use different communication protocols and/or different communication resources, such as different frequencies, time slots, spreading codes, etc.

Figure 2A:
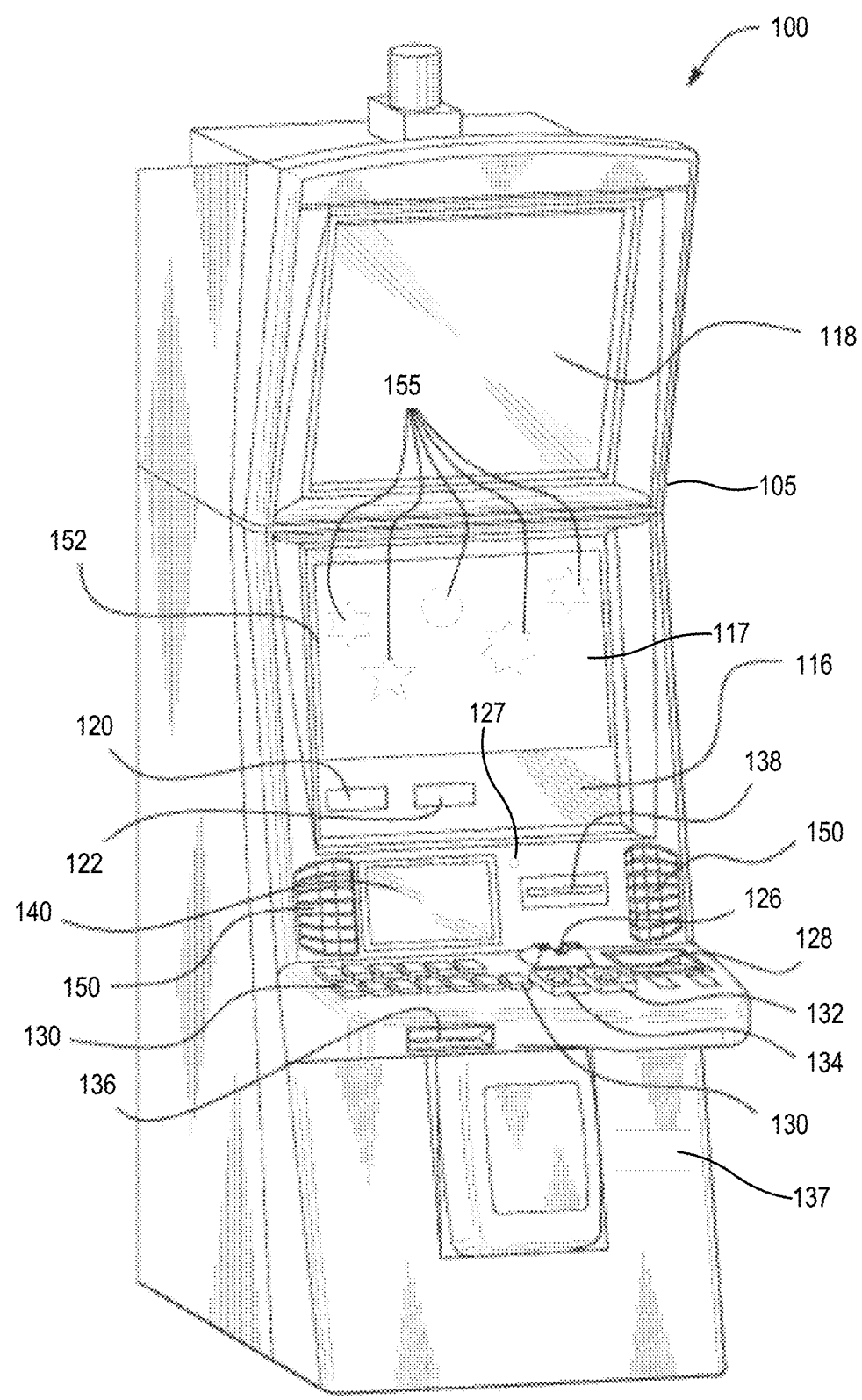
FIG. 2A is a perspective view of a gaming device that can be configured according to some embodiments.
Figure 2B:
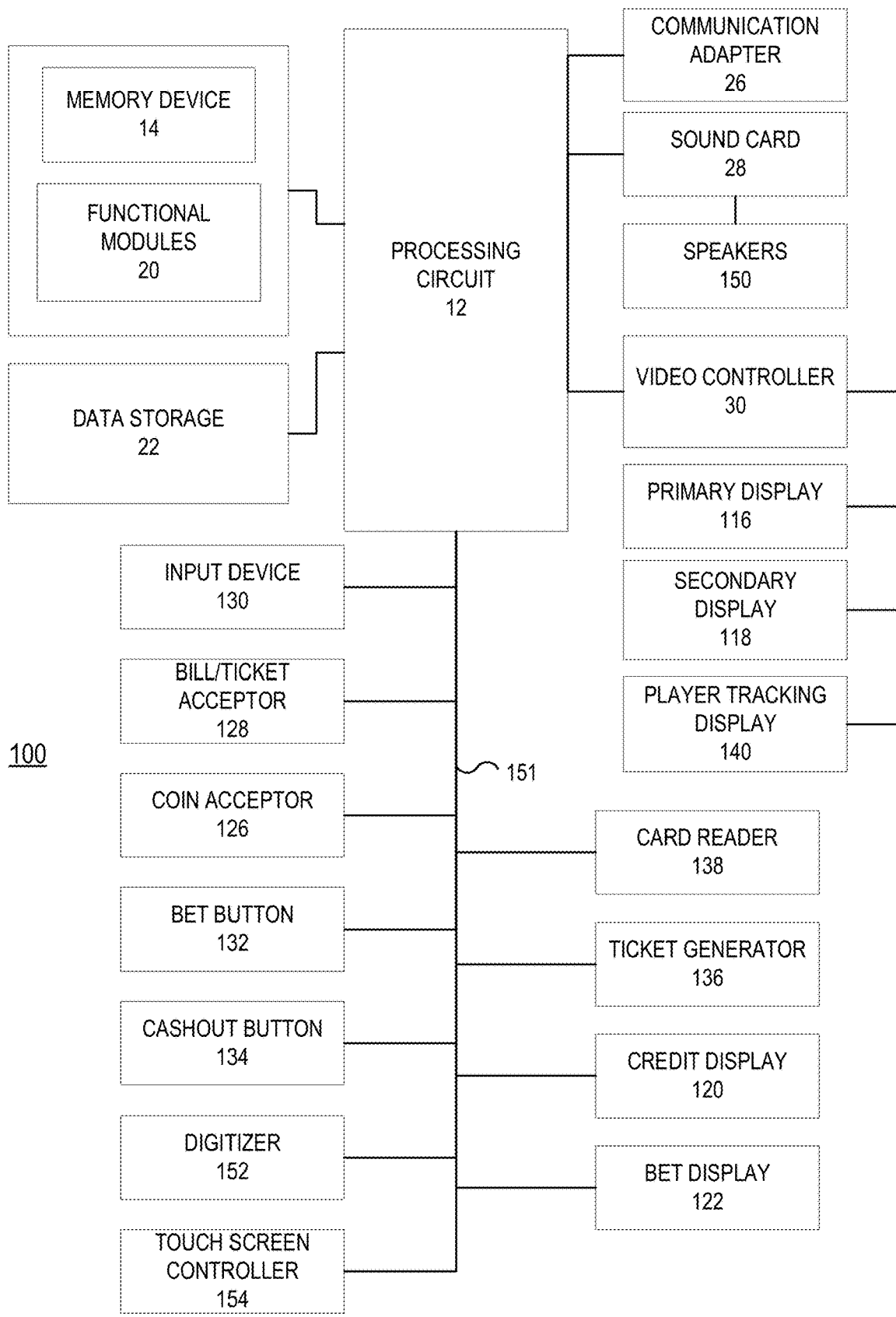
FIG. 2B is a schematic block diagram illustrating an electronic configuration for a gaming device according to some embodiments.
Figure 2C:
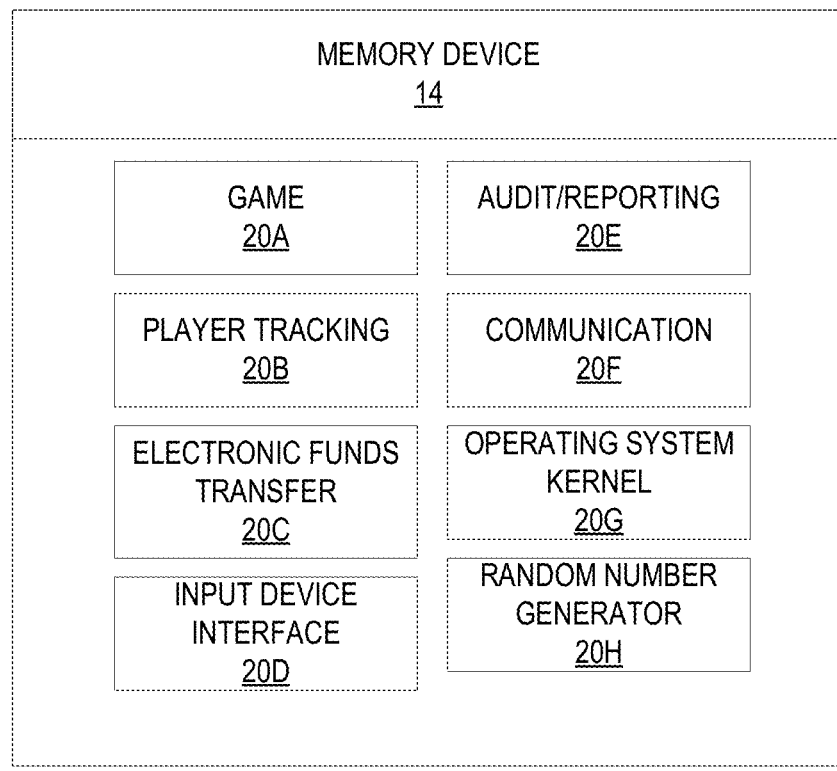
FIG. 2C is a schematic block diagram that illustrates various functional modules of a gaming device according to some embodiments.

Embodiments herein may include different types of gaming devices. One example of a gaming device includes a gaming device 100 that can use pressure and time sensitive inputs according to various embodiments is illustrated in FIGS. 2A, 2B, and 2C in which FIG. 2A is a perspective view of a gaming device 100 illustrating various physical features of the device, FIG. 2B is a functional block diagram that schematically illustrates an electronic relationship of various elements of the gaming device 100, and FIG. 2C illustrates various functional modules that can be stored in a memory device of the gaming device 100. The embodiments shown in FIGS. 2A to 2C are provided as examples for illustrative purposes only. It will be appreciated that gaming devices may come in many different shapes, sizes, layouts, form factors, and configurations, and with varying numbers and types of input and output devices, and that embodiments of the inventive concepts are not limited to the particular gaming device structures described herein.

Gaming devices 100 typically include a number of standard features, many of which are illustrated in FIGS. 2A and 2B. For example, referring to FIG. 2A, a gaming device 100 may include a support structure, housing or cabinet 105 which provides support for a plurality of displays, inputs, outputs, controls and other features that enable a player to interact with the gaming device 100.

The gaming device 100 illustrated in FIG. 2A includes a number of display devices, including a primary display device 116 located in a central portion of the cabinet 105 and a secondary display device 118 located in an upper portion of the cabinet 105. A plurality of game components 155 are displayed on a display screen 117 of the primary display device 116. It will be appreciated that one or more of the display devices 116, 118 may be omitted, or that the display devices 116, 118 may be combined into a single display device. The gaming device 100 may further include a player tracking display 140, a credit display 120, and a bet display 122. The credit display 120 displays a player's current number of credits, cash, account balance or the equivalent. The bet display 122 displays a player's amount wagered. Locations of these displays are merely illustrative as any of these displays may be located anywhere on the gaming device 100.

The player tracking display 140 may be used to display a service window that allows the player to interact with, for example, their player loyalty account to obtain features, bonuses, comps, etc. In other embodiments, additional display screens may be provided beyond those illustrated in FIG. 2A. In some embodiments, one or more of the player tracking display 140, the credit display 120 and the bet display 122 may be displayed in one or more portions of one or more other displays that display other game related visual content. For example, one or more of the player tracking display 140, the credit display 120 and the bet display 122 may be displayed in a picture in a picture on one or more displays.

The gaming device 100 may further include a number of pressure sensitive input devices 130 that allow a player to provide various inputs to the gaming device 100, either before, during or after a game has been played. The gaming device may further include a game play initiation button 132 and a cashout button 134. The cashout button 134 is utilized to receive a cash payment or any other suitable form of payment corresponding to a quantity of remaining credits of a credit display.

In some embodiments, one or more input devices of the gaming device 100 are one or more game play activation devices that are each used to initiate a play of a game on the gaming device 100 or a sequence of events associated with the gaming device 100 following appropriate funding of the gaming device 100. The example gaming device 100 illustrated in FIGS. 2A and 2B includes a game play activation device in the form of a game play initiation button 132. It should be appreciated that, in other embodiments, the gaming device 100 begins game play automatically upon appropriate funding rather than upon utilization of the game play activation device.

In some embodiments, one or more pressure sensitive input devices 130 of the gaming device 100 may include wagering or betting functionality. For example, a maximum wagering or betting function may be provided that, when utilized, causes a maximum wager to be placed. Another such wagering or betting function is a repeat the bet device that, when utilized, causes the previously-placed wager to be placed. A further such wagering or betting function is a bet one function. A bet is placed upon utilization of the bet one function. The bet is increased by one credit each time the bet one device is utilized. Upon the utilization of the bet one function, a quantity of credits shown in a credit display (as described below) decreases by one, and a number of credits shown in a bet display (as described below) increases by one.

In some embodiments, one or more of the display screens may a touch-sensitive display that includes a digitizer 152 and a touchscreen controller 154 (FIG. 2B). The player may interact with the gaming device 100 by touching virtual buttons on one or more of the display devices 116, 118, 140. Accordingly, any of the above described input devices, such as the pressure sensitive input device 130, the game play initiation button 132 and/or the cashout button 134 may be provided as virtual buttons or regions on one or more of the display devices 116, 118, 140.

Referring briefly to FIG. 2B, operation of the primary display device 116, the secondary display device 118 and the player tracking display 140 may be controlled by a video controller 30 that receives video data from a processing circuit 12 or directly from a memory device 14 and displays the video data on the display screen. The credit display 120 and the bet display 122 are typically implemented as simple LCD or LED displays that display a number of credits available for wagering and a number of credits being wagered on a particular game. Accordingly, the credit display 120 and the bet display 122 may be driven directly by the processing circuit 12. In some embodiments however, the credit display 120 and/or the bet display 122 may be driven by the video controller 30.

Referring again to FIG. 2A, the display devices 116, 118, 140 may include, without limitation: a cathode ray tube, a plasma display, a liquid crystal display (LCD), a display based on light emitting diodes (LEDs), a display based on a plurality of organic light-emitting diodes (OLEDs), a display based on polymer light-emitting diodes (PLEDs), a display based on a plurality of surface-conduction electron-emitters (SEDs), a display including a projected and/or reflected image, or any other suitable electronic device or display mechanism. In certain embodiments, as described above, the display devices 116, 118, 140 may include a touch-screen with an associated touch-screen controller 154 and digitizer 152. The display devices 116, 118, 140 may be of any suitable size, shape, and/or configuration. The display devices 116, 118, 140 may include flat or curved display surfaces.

The display devices 116, 118, 140 and video controller 30 of the gaming device 100 are generally configured to display one or more game and/or non-game images, symbols, and indicia. In certain embodiments, the display devices 116, 118, 140 of the gaming device 100 are configured to display any suitable visual representation or exhibition of the movement of objects; dynamic lighting; video images; images of people, characters, places, things, and faces of cards; and the like. In certain embodiments, the display devices 116, 118, 140 of the gaming device 100 are configured to display one or more virtual reels, one or more virtual wheels, and/or one or more virtual dice. In other embodiments, certain of the displayed images, symbols, and indicia are in mechanical form. That is, in these embodiments, the display device 116, 118, 140 includes any electromechanical device, such as one or more rotatable wheels, one or more reels, and/or one or more dice, configured to display at least one or a plurality of game or other suitable images, symbols, or indicia.

The gaming device 100 also includes various features that enable a player to deposit credits in the gaming device 100 and withdraw credits from the gaming device 100, such as in the form of a payout of winnings, credits, etc. For example, the gaming device 100 may include a ticket dispenser 136, a bill/ticket acceptor 128, and a coin acceptor 126 that allows the player to deposit coins into the gaming device 100.

As illustrated in FIG. 2A, the gaming device 100 may also include a currency dispenser 137 that may include a note dispenser configured to dispense paper currency and/or a coin generator configured to dispense coins or tokens in a coin payout tray.

The gaming device 100 may further include one or more speakers 150 controlled by one or more sound cards 28 (FIG. 2B). The gaming device 100 illustrated in FIG. 2A includes a pair of speakers 150. In other embodiments, additional speakers, such as surround sound speakers, may be provided within or on the cabinet 105. Moreover, the gaming device 100 may include built-in seating with integrated headrest speakers.

In various embodiments, the gaming device 100 may generate dynamic sounds coupled with attractive multimedia images displayed on one or more of the display devices 116, 118, 140 to provide an audio-visual representation or to otherwise display full-motion video with sound to attract players to the gaming device 100 and/or to engage the player during gameplay. In certain embodiments, the gaming device 100 may display a sequence of audio and/or visual attraction messages during idle periods to attract potential players to the gaming device 100. The videos may be customized to provide any appropriate information.

The gaming device 100 may further include a card reader 138 that is configured to read magnetic stripe cards, such as player loyalty/tracking cards, chip cards, and the like. In some embodiments, a player may insert an identification card into a card reader of the gaming device. In some embodiments, the identification card is a smart card having a programmed microchip or a magnetic strip coded with a player's identification, credit totals (or related data) and other relevant information. In other embodiments, a player may carry a portable device, such as a cell phone, a radio frequency identification tag or any other suitable wireless device, which communicates a player's identification, credit totals (or related data) and other relevant information to the gaming device. In some embodiments, money may be transferred to a gaming device through electronic funds transfer. When a player funds the gaming device, the processing circuit determines the amount of funds entered and displays the corresponding amount on the credit or other suitable display as described above.

In some embodiments, the gaming device 100 may include an electronic payout device or module configured to fund an electronically recordable identification card or smart card or a bank or other account via an electronic funds transfer to or from the gaming device 100.

FIG. 2B is a block diagram that illustrates logical and functional relationships between various components of a gaming device 100. It should also be understood that components described in FIG. 2B may also be used in other computing devices, as desired, such as mobile computing devices for example. As shown in FIG. 2B, the gaming device 100 may include a processing circuit 12 that controls operations of the gaming device 100. Although illustrated as a single processing circuit, multiple special purpose and/or general purpose processors and/or processor cores may be provided in the gaming device 100. For example, the gaming device 100 may include one or more of a video processor, a signal processor, a sound processor and/or a communication controller that performs one or more control functions within the gaming device 100. The processing circuit 12 may be variously referred to as a "controller," "microcontroller," "microprocessor" or simply a "computer." The processor may further include one or more application-specific integrated circuits (ASICs).

Various components of the gaming device 100 are illustrated in FIG. 2B as being connected to the processing circuit 12. It will be appreciated that the components may be connected to the processing circuit 12 through a system bus, a communication bus and controller, such as a USB controller and USB bus, a network interface, or any other suitable type of connection.

The gaming device 100 further includes a memory device 14 that stores one or more functional modules 20. Various functional modules 20 of the gaming device 100 will be described in more detail below in connection with FIG. 2D.

The memory device 14 may store program code and instructions, executable by the processing circuit 12, to control the gaming device 100. The memory device 14 may also store other data such as image data, event data, player input data, random or pseudo-random number generators, pay-table data or information and applicable game rules that relate to the play of the gaming device. The memory device 14 may include random access memory (RAM), which can include non-volatile RAM (NVRAM), magnetic RAM (ARAM), ferroelectric RAM (FeRAM) and other forms as commonly understood in the gaming industry. In some embodiments, the memory device 14 may include read only memory (ROM). In some embodiments, the memory device 14 may include flash memory and/or EEPROM (electrically erasable programmable read only memory). Any other suitable magnetic, optical and/or semiconductor memory may operate in conjunction with the gaming device disclosed herein.

The gaming device 100 may further include a data storage device 22, such as a hard disk drive or flash memory. The data storage 22 may store program data, player data, audit trail data or any other type of data. The data storage 22 may include a detachable or removable memory device, including, but not limited to, a suitable cartridge, disk, CD ROM, DVD or USB memory device.

The gaming device 100 may include a communication adapter 26 that enables the gaming device 100 to communicate with remote devices over a wired and/or wireless communication network, such as a local area network (LAN), wide area network (WAN), cellular communication network, or other data communication network. The communication adapter 26 may further include circuitry for supporting short range wireless communication protocols, such as Bluetooth and/or near field communications (NFC) that enable the gaming device 100 to communicate, for example, with a mobile communication device operated by a player.

The gaming device 100 may include one or more internal or external communication ports that enable the processing circuit 12 to communicate with and to operate with internal or external peripheral devices, such as eye tracking devices, position tracking devices, cameras, accelerometers, arcade sticks, bar code readers, bill validators, biometric input devices, bonus devices, button panels, card readers, coin dispensers, coin hoppers, display screens or other displays or video sources, expansion buses, information panels, keypads, lights, mass storage devices, microphones, motion sensors, motors, printers, reels, SCSI ports, solenoids, speakers, thumb drives, ticket readers, touch screens, trackballs, touchpads, wheels, and wireless communication devices. In some embodiments, internal or external peripheral devices may communicate with the processing circuit through a universal serial bus (USB) hub (not shown) connected to the processing circuit 12.

In some embodiments, the gaming device 100 may include a sensor, such as a camera in communication with the processing circuit 12 (and possibly controlled by the processing circuit 12) that is selectively positioned to acquire an image of a player actively using the gaming device 100 and/or the surrounding area of the gaming device 100. In one embodiment, the camera may be configured to selectively acquire still or moving (e.g., video) images and may be configured to acquire the images in either an analog, digital or other suitable format. The display devices 116, 118, 140 may be configured to display the image acquired by the camera as well as display the visible manifestation of the game in split screen or picture-in-picture fashion. For example, the camera may acquire an image of the player and the processing circuit 12 may incorporate that image into the primary and/or secondary game as a game image, symbol or indicia.

Various functional modules of that may be stored in a memory device 14 of a gaming device 100 are illustrated in FIG. 2C. Referring to FIG. 2C, the gaming device 100 may include in the memory device 14 a game module 20A that includes program instructions and/or data for operating a hybrid wagering game as described herein. The gaming device 100 may further include a player tracking module 20B, an electronic funds transfer module 20C, an input device interface 20D, an audit/reporting module 20E, a communication module 20F, an operating system 20G and a random number generator 20H. The player tracking module 20B keeps track of the play of a player. The electronic funds transfer module 20C communicates with a back-end server or financial institution to transfer funds to and from an account associated with the player. The input device interface 20D interacts with input devices, such as the pressure sensitive input device 130, as described in more detail below. The communication module 20F enables the gaming device 100 to communicate with remote servers and other gaming devices using various secure communication interfaces. The operating system kernel 20G controls the overall operation of the gaming device 100, including the loading and operation of other modules. The random number generator 20H generates random or pseudorandom numbers for use in the operation of the hybrid games described herein.

In some embodiments, a gaming device 100 comprises a personal device, such as a desktop computer, a laptop computer, a mobile device, a tablet computer or computing device, a personal digital assistant (PDA), or other portable computing devices. In some embodiments, the gaming device 100 may be operable over a wireless network, such as part of a wireless gaming system. In such embodiments, the gaming machine may be a hand-held device, a mobile device or any other suitable wireless device that enables a player to play any suitable game at a variety of different locations. It should be appreciated that a gaming device or gaming machine as disclosed herein may be a device that has obtained approval from a regulatory gaming commission or a device that has not obtained approval from a regulatory gaming commission.

Figure 2D:
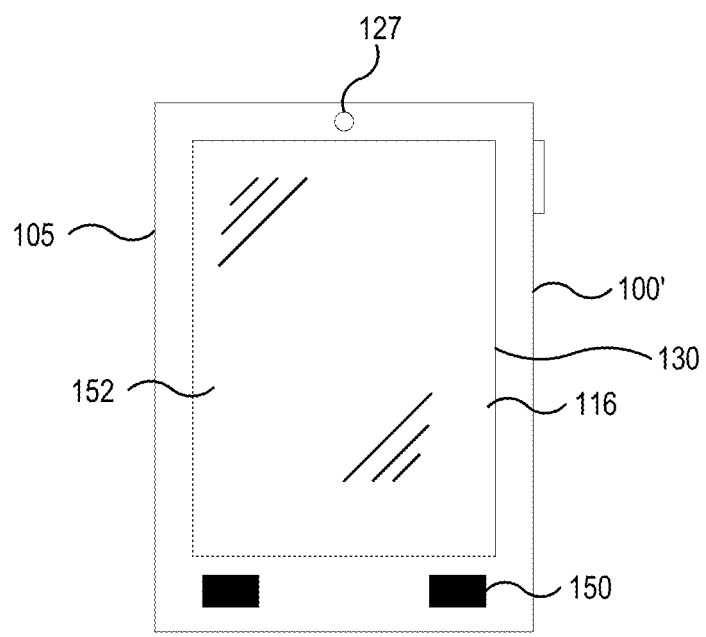
FIG. 2D is perspective view of a gaming device that can be configured according to some embodiments.

For example, referring to FIG. 2D, a gaming device 100' may be implemented as a handheld device including a compact housing 105 on which is mounted a touchscreen display device 116 including a digitizer 152. As described in greater detail with respect to FIG. 3 below, one or more pressure sensitive input devices 130 may be included for providing functionality of for embodiments described herein. A camera 127 may be provided in a front face of the housing 105. The housing 105 may include one or more speakers 150. In the gaming device 100', various input buttons described above, such as the cashout button, game-play activation button, etc., may be implemented as soft buttons on the touchscreen display device 116 and/or pressure sensitive input device 130. In this embodiment, the pressure sensitive input device 130 is integrated into the touchscreen display device 116, but it should be understood that the pressure sensitive input device may also, or alternatively, be separate from the display device 116. Moreover, the gaming device 100' may omit certain features, such as a bill acceptor, a ticket generator, a coin acceptor or dispenser, a card reader, secondary displays, a bet display, a credit display, etc. Credits can be deposited in or transferred from the gaming device 100' electronically.

Figure 2E:
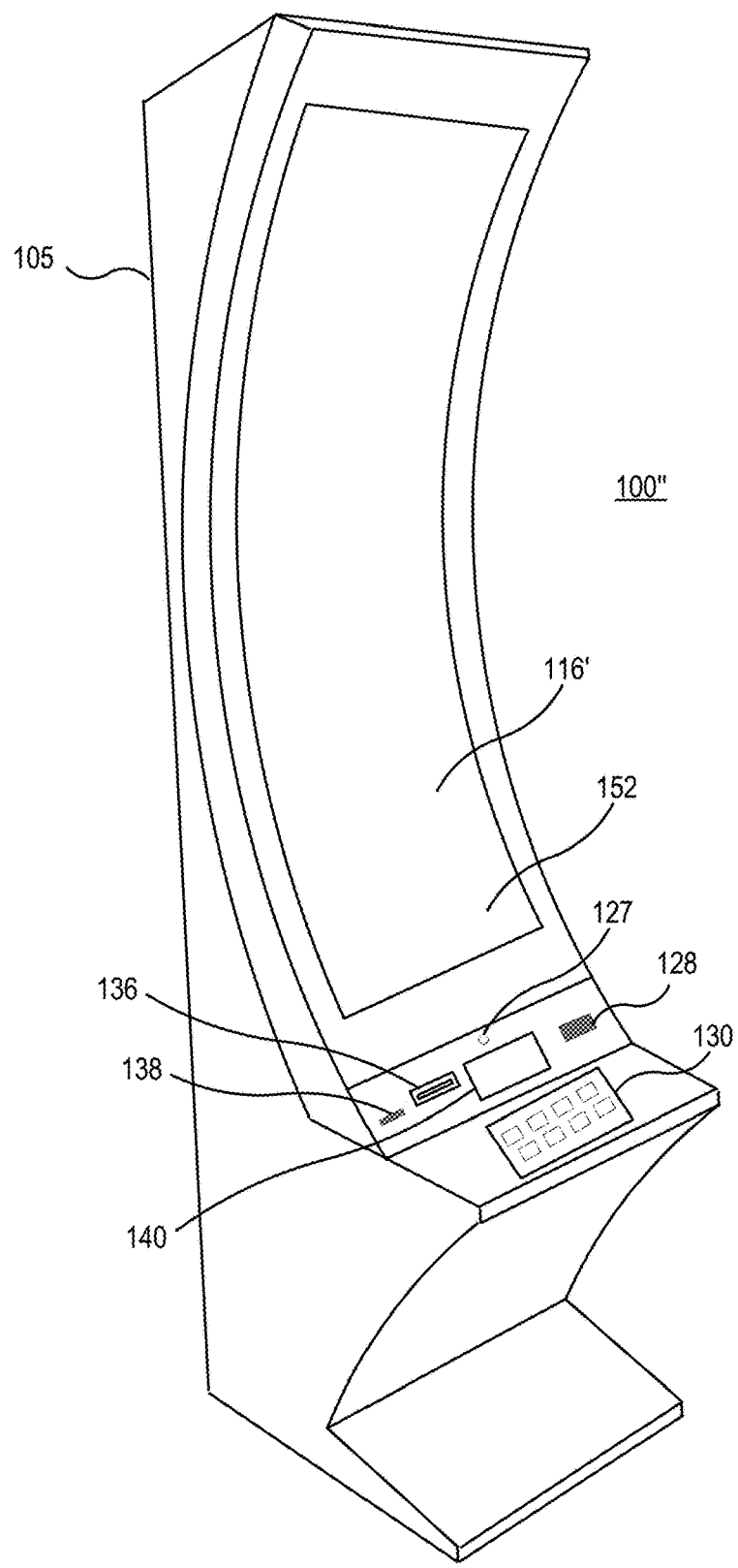
FIG. 2E is a perspective view of a gaming device according to further embodiments.

FIG. 2E illustrates a standalone gaming device 100" having a different form factor from the gaming device 100 illustrated in FIG. 2A. In particular, the gaming device 100" is characterized by having a large, high aspect ratio, curved primary display device 116' provided in the housing 105, with no secondary display device. The primary display device 116' may include a digitizer 152 to allow touchscreen interaction with the primary display device 116'. The gaming device 100" may further include a player tracking display 140, a pressure sensitive input device 130, a bill/ticket acceptor 128, a card reader 138, and a ticket generator 136. The gaming device 100" may further include one or more cameras 127 to enable facial recognition and/or motion tracking.

Although illustrated as certain gaming devices, such as electronic gaming machines (EGMs) and mobile devices, similar functions and/or operations as described herein may include wagering stations that may include electronic game tables, conventional game tables including those involving cards, dice and/or roulette, and/or other wagering stations such as sports book stations, video poker games, skill-based games, virtual casino-style table games, or other casino or non-casino style games. Further, gaming devices according to embodiments herein may be implemented using other computing devices and mobile devices, such as smart phones, tablets, and/or personal computers, among others.

Figure 3:
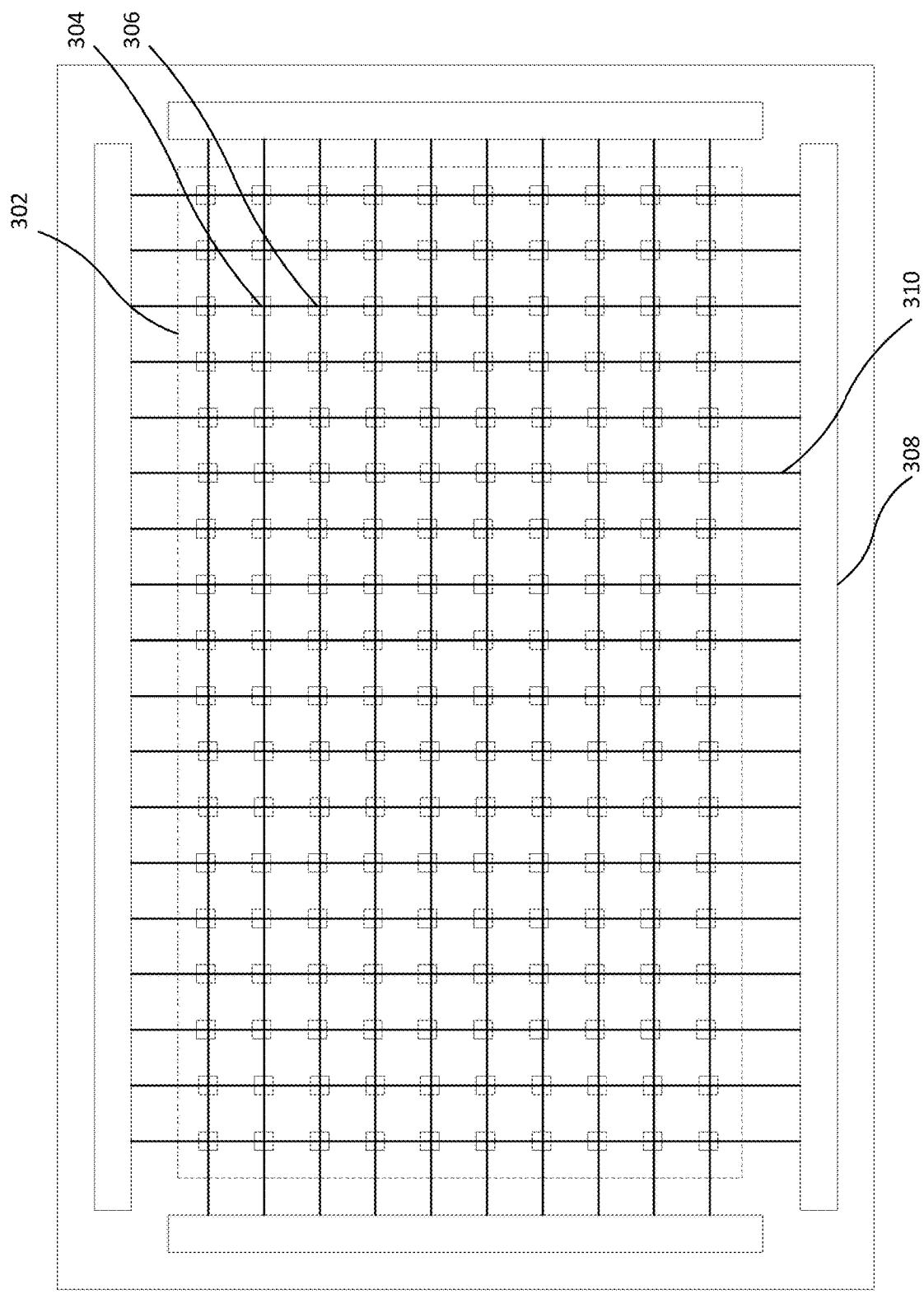
FIG. 3 is a schematic diagram that illustrates various components of an input device according to some embodiments.

Referring now to FIG. 3, a schematic diagram of components of a pressure sensitive input device 130 is are illustrated, according to some embodiments. The pressure sensitive input device 130 includes a printed circuit board 302 having a two-dimensional array of sensor locations 304. A pressure sensitive sensor 306 is located at each sensor location 304 to detect an amount of pressure being applied to the particular sensor location 304, e.g., by a player applying pressure to the sensor location 304 as part of game play. The pressure sensitive sensor 306 may function in a variety of ways. In this example, the pressure sensitive sensors 306 are coupled to one or more controller circuits 308 via one or more conductive lines 310.

In some embodiments, the conductive lines 310 and controller circuit 308 may also, or alternatively, provide capacitive and/or resistive touch screen and/or touch pad functionality. For example, the controller circuits 308 may determine a sensor location 304 through an increase in capacitance of particular conductive lines 310 that intersect at the particular sensor location 304, caused by the player applying pressure to the particular sensor location 304. In another example, the player applying pressure to the particular sensor location 304 may cause the conductive lines that intersect at the particular sensor location 304 to contact each other and conduct a current between the controller circuits 308. In some examples, one or more individual pressure sensitive sensors 306 may associated with each respective sensor location 304, with each individual pressure sensitive sensor 306 independently detecting pressure being applied at the particular sensor location 304. Additional functionality may also include providing feedback, such as audio, visual, and/or haptic feedback, based on an amount of detected pressure at a particular sensor location 304.

It should be understood that a wide variety of pressure sensitive sensors and/or input devices may be used to provide features and functionality described herein. For example, one suitable pressure sensitive input device for many embodiments described herein is the Sensel Morph touch interface, which includes an active area having an array of approximately 20,000 pressure sensors at a density of approximately 6500 sensors per inch. Each sensor is capable of sensing 32,000 levels of pressure in a range between 5 g and 5 kg. The interface can operate at different speeds and latencies, such as a full resolution mode at 125 Hz, which provides greater precision but higher latency (e.g., 8 ms), or a higher speed, lower resolution mode at 500 Hz, which provides lower latency (e.g., 2 ms) but with lower precision.

Some embodiments provide that human-machine interactions may be improved by providing a pressure-sensitive multi-touch input at gaming devices 100 to offer users more control and additional functionalities. Some embodiments may be further enhanced by including haptic feedback corresponding to a pressure-sensitive multi-touch input and based on the amount and/or duration of pressure applied thereto.

Embodiments herein may address a technical problem of not realizing a player's emotional state and thus the player's level of satisfaction with the gaming experience by providing an ability to use a pressure sensitive input device during gameplay to draw conclusions regarding the player's emotional state and by modifying the game play and/or experience to increase the player's satisfaction. For example, some embodiments provide that touch properties such as pressure strength, pressure length, stroke length, stroke direction and stroke speed, along with game situations, may be used to evaluate a player's emotional state.

For example, a strong pressing during a sustained winning streak may be interpreted to indicate that the player is excited. In contrast, a strong pressing during a losing streak may indicate that a player is frustrated or angry. A soft pressing during a gaming session may indicate that the player is relaxed. In some embodiments, a player trying to skip or avoid unnecessary game explanations may repeatedly apply increasing pressure during rapid pressing. Such activities may indicate that the player is impatient. Some embodiments provide that continuous or delayed pressing may indicate that the player is bored or that the game events are perceived as unspectacular. A player hesitantly or tentatively pressing may indicate insecurity and/or that the player is overwhelmed with a decision.

Based on the evaluations of the player, the gaming machine 100 may react specifically in certain game situations. In some embodiments, within the game, the player may be trained to press softly when they like an event and harder if they don't like an event. Some embodiments provide that players, by playing, may be providing feedback to certain events and/or other game features. Such information may provide game evaluation data for game providers to determine which features are more or less popular.

In some embodiments, the accuracy of the pressing may indicate player focus, distractions, and/or emotional states. For example, a pressing that occurs and/or moves to an area that is outside a designated area may indicate that a player is distracted and/or impaired due to fatigue and/or consumption of an impairing substance.

Some embodiments provide that the received pressure data may be used in combination with other technologies that may be used to evaluate a player's emotional state. Such technologies, when used in combination with received pressure data may improve accuracy of the evaluation of the player's emotional state. Non-limiting examples of such technologies include facial emotional state detection, pupil dilation/movement, and/or biometric sensors, among others.

Embodiments herein may use a measure of how hard a button that is defined on the pressure sensitive input device 130 is pressed and determine a correlation between the user and the game. For example, some embodiments provide that the harder the button is pressed, the higher the aggression level of the player in playing the game. In some embodiments, it may be determined that the player may be demotivated when hitting the button harder due to losing streak. The game play may be modified to provide a win to the player.

In some embodiments, responsive to the player pressing a button using less force, which may be determined as the payer having less aggression, the short-term return to player may be decreased and money may be saved back from the player. In such embodiments, the saved back money may be paid out during losing streaks in response to determining that the player is in a negative emotional state based on the harder pressing of inputs at the pressure sensitive input device 130. Such game modification may improve the player's emotional state.

In some embodiments, a determination of the player's emotional state may be made based on the frequency and pressure of the pressing. Some embodiments provide that game speed may be adjusted automatically based on player's pressure, frequency and/or speed of interfacing with the pressure sensitive input device 130. For example, in response to the player pressing hard and highly frequently, which may indicate impatience by the player, the game speed may be automatically increased. In contrast, in response to the player pressing slower and with less frequency, the game speed may be automatically adjusted to be slower and/or to show game presentations for a longer period of time. In some embodiments, in response to a player pressing bet button increasingly faster and steadier, game speed may be automatically increased to go faster than a fast reel stop mode. In some embodiments, in a game tutorial in which the player is pressing the pressure sensitive input device 130 hard and at a high frequency, the tutorial and/or portions thereof may be skipped and/or delivered more quickly relative to when the pressure sensitive input device 130 is being pressed more softly and/or at a lower frequency.

In some embodiments, the player may be allowed to perceive influence in the game based on how they press the pressure sensitive input device 130. For example, the spin duration of a tension spin may be increased in response to the player pressing harder and/or more frequently to further increase the player's tension.

In some embodiments, the pressure sensitive input device 130 may use pressure, movement and/or touch patterns to determine a player's emotional state corresponding to decision points in the game. For example, it may be determined that a player is overwhelmed or confused based on very soft and/or hesitant pressing at the pressure sensitive input device 130. In such cases, the game may be automatically modified to provide additional instructions, such as tutorials, and or to provide hints to the player.

Some embodiments provide that, while a player is interacting with a game, features derived from stroke length, stroke direction, stroke speed, and pressure can be used to identify at least four different emotional states, including excited, relaxed, frustrated and bored. Game play may be modified according to the player state. For example, in some embodiments, a new game could be recommended if the player is bored.

Embodiments described herein may be implemented in various configurations for gaming devices 100, including but not limited to: (1) a dedicated gaming device, wherein the computerized instructions for controlling any games (which are provided by the gaming device) are provided with the gaming device prior to delivery to a gaming establishment; and (2) a changeable gaming device, where the computerized instructions for controlling any games (which are provided by the gaming device) are downloadable to the gaming device through a data network when the gaming device is in a gaming establishment. In some embodiments, the computerized instructions for controlling any games are executed by at least one central server, central controller or remote host. In such a "thin client" embodiment, the central server remotely controls any games (or other suitable interfaces) and the gaming device is utilized to display such games (or suitable interfaces) and receive one or more inputs or commands from a player. In another embodiment, the computerized instructions for controlling any games are communicated from the central server, central controller or remote host to a gaming device local processor and memory devices. In such a "thick client" embodiment, the gaming device local processor executes the communicated computerized instructions to control any games (or other suitable interfaces) provided to a player.

In some embodiments, a gaming device may be operated by a mobile device, such as a mobile telephone, tablet other mobile computing device. For example, a mobile device may be communicatively coupled to a gaming device and may include a user interface that receives user inputs that are received to control the gaming device. The user inputs may be received by the gaming device via the mobile device.

In some embodiments, one or more gaming devices in a gaming system may be thin client gaming devices and one or more gaming devices in the gaming system may be thick client gaming devices. In another embodiment, certain functions of the gaming device are implemented in a thin client environment and certain other functions of the gaming device are implemented in a thick client environment. In one such embodiment, computerized instructions for controlling any primary games are communicated from the central server to the gaming device in a thick client configuration and computerized instructions for controlling any secondary games or bonus functions are executed by a central server in a thin client configuration.

The present disclosure contemplates a variety of different gaming systems each having one or more of a plurality of different features, attributes, or characteristics. It should be appreciated that a "gaming system" as used herein refers to various configurations of: (a) one or more central servers, central controllers, or remote hosts; (b) one or more gaming devices; and/or (c) one or more personal gaming devices, such as desktop computers, laptop computers, tablet computers or computing devices, personal digital assistants (PDAs), mobile telephones such as smart phones, and other mobile computing devices.

In certain such embodiments, computerized instructions for controlling any games (such as any primary or base games and/or any secondary or bonus games) displayed by the gaming device are executed by the central server, central controller, or remote host. In such "thin client" embodiments, the central server, central controller, or remote host remotely controls any games (or other suitable interfaces) displayed by the gaming device, and the gaming device is utilized to display such games (or suitable interfaces) and to receive one or more inputs or commands. In other such embodiments, computerized instructions for controlling any games displayed by the gaming device are communicated from the central server, central controller, or remote host to the gaming device and are stored in at least one memory device of the gaming device. In such "thick client" embodiments, the at least one processor of the gaming device executes the computerized instructions to control any games (or other suitable interfaces) displayed by the gaming device.

In some embodiments in which the gaming system includes: (a) a gaming device configured to communicate with a central server, central controller, or remote host through a data network; and/or (b) a plurality of gaming devices configured to communicate with one another through a data network, the data network is an internet or an intranet. In certain such embodiments, an internet browser of the gaming device is usable to access an internet game page from any location where an internet connection is available. In one such embodiment, after the internet game page is accessed, the central server, central controller, or remote host identifies a player prior to enabling that player to place any wagers on any plays of any wagering games. In one example, the central server, central controller, or remote host identifies the player by requiring a player account of the player to be logged into via an input of a unique username and password combination assigned to the player. It should be appreciated, however, that the central server, central controller, or remote host may identify the player in any other suitable manner, such as by validating a player tracking identification number associated with the player; by reading a player tracking card or other smart card inserted into a card reader (as described below); by validating a unique player identification number associated with the player by the central server, central controller, or remote host; or by identifying the gaming device, such as by identifying the MAC address or the IP address of the internet facilitator. In various embodiments, once the central server, central controller, or remote host identifies the player, the central server, central controller, or remote host enables placement of one or more wagers on one or more plays of one or more primary or base games and/or one or more secondary or bonus games, and displays those plays via the internet browser of the gaming device.

It should be appreciated that the central server, central controller, or remote host and the gaming device are configured to connect to the data network or remote communications link in any suitable manner. In various embodiments, such a connection is accomplished via: a conventional phone line or other data transmission line, a digital subscriber line (DSL), a T-1 line, a coaxial cable, a fiber optic cable, a wireless or wired routing device, a mobile communications network connection (such as a cellular network or mobile internet network), or any other suitable medium. It should be appreciated that the expansion in the quantity of computing devices and the quantity and speed of internet connections in recent years increases opportunities for players to use a variety of gaming devices to play games from an ever-increasing quantity of remote sites. It should also be appreciated that the enhanced bandwidth of digital wireless communications may render such technology suitable for some or all communications, particularly if such communications are encrypted. Higher data transmission speeds may be useful for enhancing the sophistication and response of the display and interaction with players.

By providing pressure sensitive input features, human machine interactions between players and gaming devices may be enhanced by offering players additional control and functionalities. Such functionality may include pushing the input device at a particular sensor location to exceed a defined pressure threshold and generate a response, such as a haptic response for example. This functionality may simulate pressing physical buttons or interaction with other mechanical devices in some examples.

In some examples, a detected amount of pressure at a particular sensor location may be combined with other pressure parameter values to determine a player's emotional state while playing the gaming device. For example, a pressure sensitive input device 130 herein includes multiple input locations and a pressure sensor to detect, for each input location, an amount of pressure applied by a player to the pressure sensitive input device 130 at the input location of the gaming device.

Figure 4:
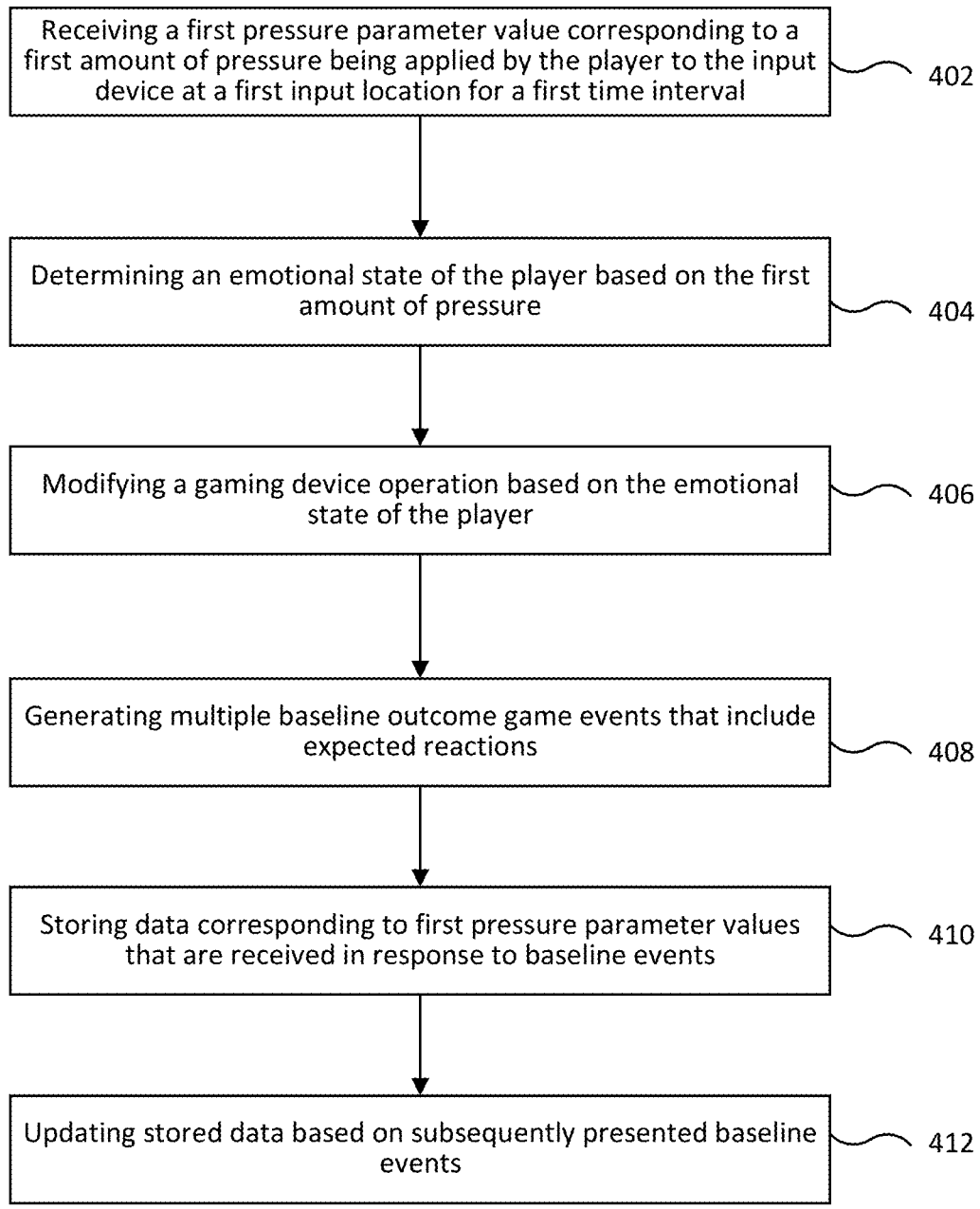
FIG. 4 is a flowchart illustrating operations of systems/methods according to some embodiments.

In this regard, reference is now made to FIG. 4, which is a flowchart illustrating operations 400 of systems/methods according to some embodiments. The operations 400 may include receiving, from the pressure sensor, a first pressure parameter value corresponding to a first amount of pressure being applied by the player to the input device at a first input location (block 402). In some embodiments, the pressure may be applied for a first time interval that lasts for a first time duration.

In some embodiments, the input location corresponds to a graphic of a user input element that receives inputs for the gaming device. In response receiving the first pressure parameter value for a given period of time, a haptic response may be generated at the input location of the gaming device.

Operations include determining, based on the first amount of pressure being applied to the pressure sensor, an emotional state of the player (block 404). For example, a player in a generally negative state may apply more pressure to the pressure sensor than a player in a generally positive state. Some embodiments provide that multiple first pressure parameter values may be received. In some embodiments, operations may determine a speed of player inputs based on multiple first pressure parameter values. Some embodiments provide that determining the emotional state is based on the first time duration among other factors.

An operation of the gaming device may be modified based on the emotional state of the player (block 406). For example, some embodiments provide that the game pace and/or winning occurrences may be automatically adjusted in response to the determined emotional state of the player.

In some embodiments, operations include generating multiple baseline outcome game events that include expected reactions thereto (block 408). In response to the baseline outcome game events, data corresponding to the first pressure parameter values may be received and may be stored as baseline pressure parameter values that are associated with the respective ones of the baseline outcome game events (block 410).

By storing pressure value data corresponding to different baseline outcome game events, changes in the emotional state of the player may be determined. For example, determining the emotional state of the player may be performed by determine a pressure difference between subsequently received first pressure parameter values to the baseline pressure parameter values. In such embodiments, one or more operations of the gaming device may be modified based on the pressure difference exceeding a pre-defined pressure difference threshold.

In some embodiments, operations may include updating the stored data corresponding to the first pressure parameter values based on subsequently presented baseline outcome game events (block 412). In this manner, determining the emotional state of the player may be determined relative to more recently occurring conditions by using more recently received first pressure parameter values.

It should also be understood that devices and systems described herein may perform some or all of the disclosed operations 400. For example, a gaming device 100 of FIGS. 2A-2E above may have an input device, a processor circuit, and a memory to perform these and similar operations.

Figure 5:
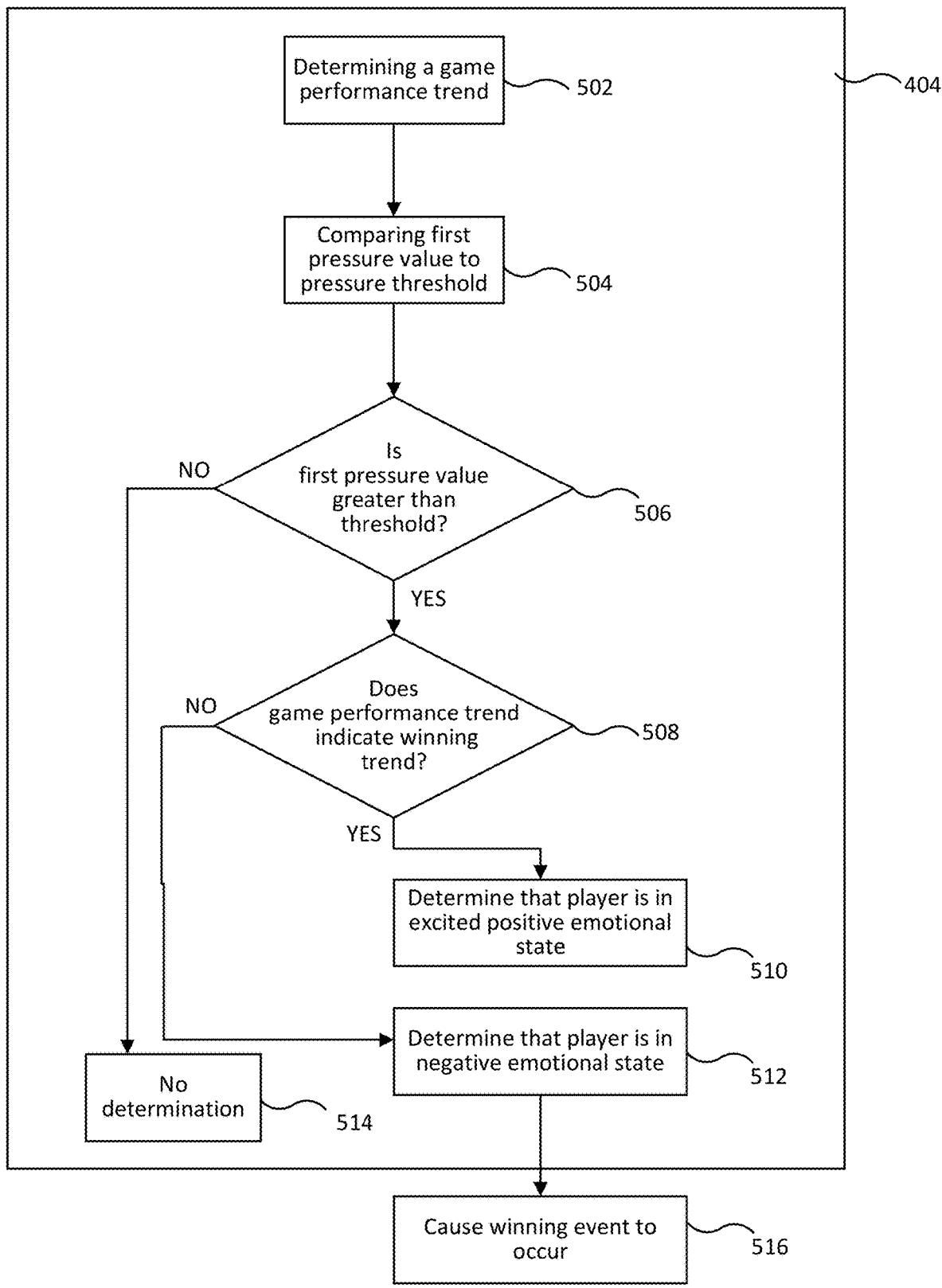
FIG. 5 is a flowchart illustrating operations of systems/methods according to some embodiments.

Reference is now made to FIG. 5, which is a flowchart illustrating operations corresponding to determining the emotional state of a player (block 404) according to some embodiments. According to some embodiments, determining the emotional state includes determining a game performance trend that corresponds to player winning history data (block 502). For example, the winning history data may correspond to a recent time interval and/or may be based on a recent number of plays and/or rounds of play. Operations include comparing the first pressure parameter value to a pressure parameter threshold (block 504). Based on the comparing operation, operations of block 506 determine if the first pressure parameter value is greater than the pressure parameter threshold. If the first pressure parameter is not greater than the pressure parameter threshold, then no determination regarding the emotional state of the player may be made (block 514). If the first pressure parameter value is greater than the pressure parameter threshold, the operations may determine is the game performance trend indicates a winning trend (block 508). In response to the game performance trend indicating that the player has a winning history over a given previous time period and/or number of plays, operations may determine that the player is in an excited positive emotional state (block 510). In contrast, if the first pressure parameter value is greater than the pressure parameter threshold and the game performance trend indicates that the player has a losing history over a given previous time period and/or number of plays, the operations may determine that the player is in a negative emotional state (block 512).

In some embodiments, in responsive to determining that the player is in a negative emotional state, the operation of the gaming device may be modified to cause a winning event to occur corresponding to a game on the gaming device (block 516).

Figure 6:
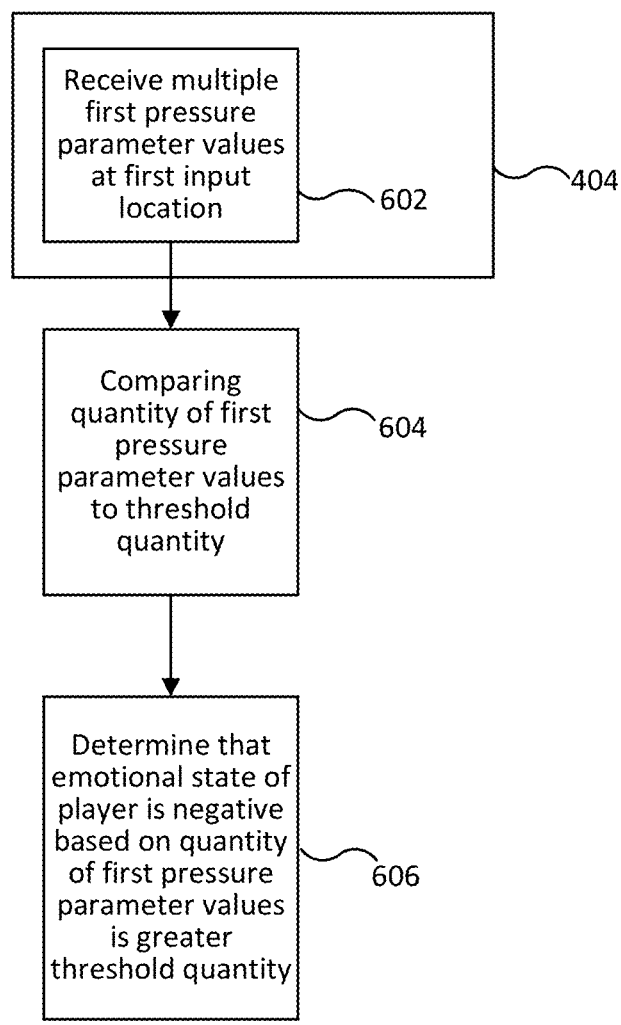
FIG. 6 is a flowchart illustrating operations of systems/methods according to some embodiments.

Reference is now made to FIG. 6, which is a flowchart illustrating operations of systems/methods according to some embodiments. In some embodiments, the first input location of the pressure sensitive input device 130 corresponds to a graphic of a user input element that receives inputs for the gaming device. For example, a graphic corresponding to a push button or other user interface element may be provided in the first input location. In such embodiments, receiving the first pressure parameter value (block 402) includes receiving multiple first pressure parameter values at the first input location in a given period of time (block 602). For example, a given period of time may correspond to an amount of time in which the player is expected to provide an input.

Some embodiments provide operations include comparing a quantity of the first pressure parameter values that are received during the given time period to a threshold quantity of values corresponding to the given time period (block 604). In some embodiments, an excessive number of button pushes in a given time period may be indicative of the emotional state of the player. For example, based on the quantity of first pressure parameter values being greater than the threshold quantity of values, operations may include determining that the emotional state of the player is negative (block 606). The negative emotional state may correspond to impatience, frustration and/or an agitated emotional state.

Figure 7:
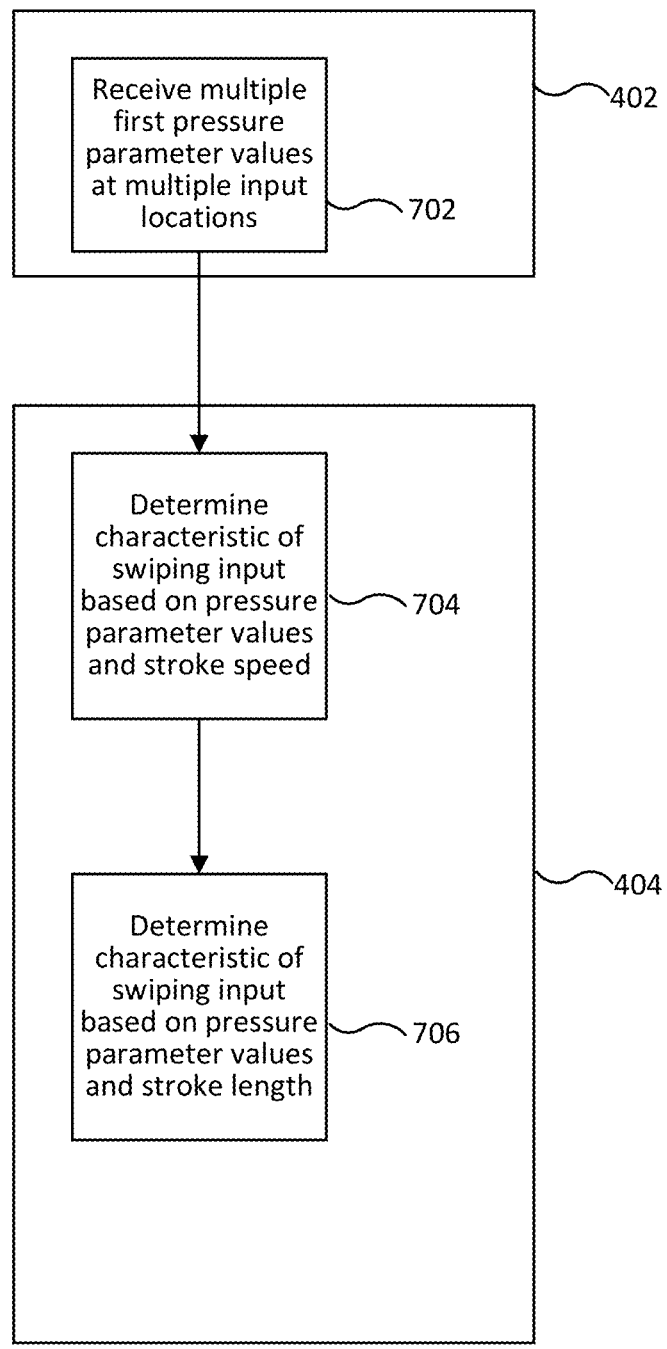
FIG. 7 is a flowchart illustrating operations of systems/methods according to some embodiments.

Reference is now made to FIG. 7, which is a flowchart illustrating operations of systems/methods according to some embodiments. Some embodiments provide that the input location includes multiple input locations that correspond to a swiping input from the player. In some embodiments, receiving the first pressure parameter value (block 402) includes receiving multiple pressure parameter values at respective ones of the multiple input locations (block 702). Such embodiments may also determine the stroke speed of the swiping input based on the timing between the multiple pressure parameter values and the stroke length of the swiping input based on which of the plurality of input locations receive pressure inputs.

In such embodiments, determining the emotional state (block 404) includes determining a characteristic of the swiping input based on the multiple pressure parameter values and the swiping stroke speed of the swiping input (block 704). In some embodiments, the emotional state of the player is determined based on changes in the swiping stroke speed over a given time interval. In response to the swiping stroke speed increasing over the given time interval, modifying the operation of the gaming device may cause an increase in the speed of game play. In response to the swiping stroke speed decreasing over the given time interval, modifying the operation of the gaming device may cause a decrease in the speed of game play.

In some embodiments, determining the emotional state (block 404) includes determining a characteristic of the swiping input based on the multiple pressure parameter values and the swiping stroke length of the swiping input (block 706). Some embodiments provide that the emotional state of the player is determined based on changes in the swiping stroke length. For example, in response to the swiping stroke length increasing over a given time interval, modifying the operation of the gaming device may include causing a decrease in the speed of game play. In other cases, in response to the swiping stroke length decreasing over the given time interval, modifying the operation of the gaming device may include causing an increase in the speed of game play.

Figure 8:
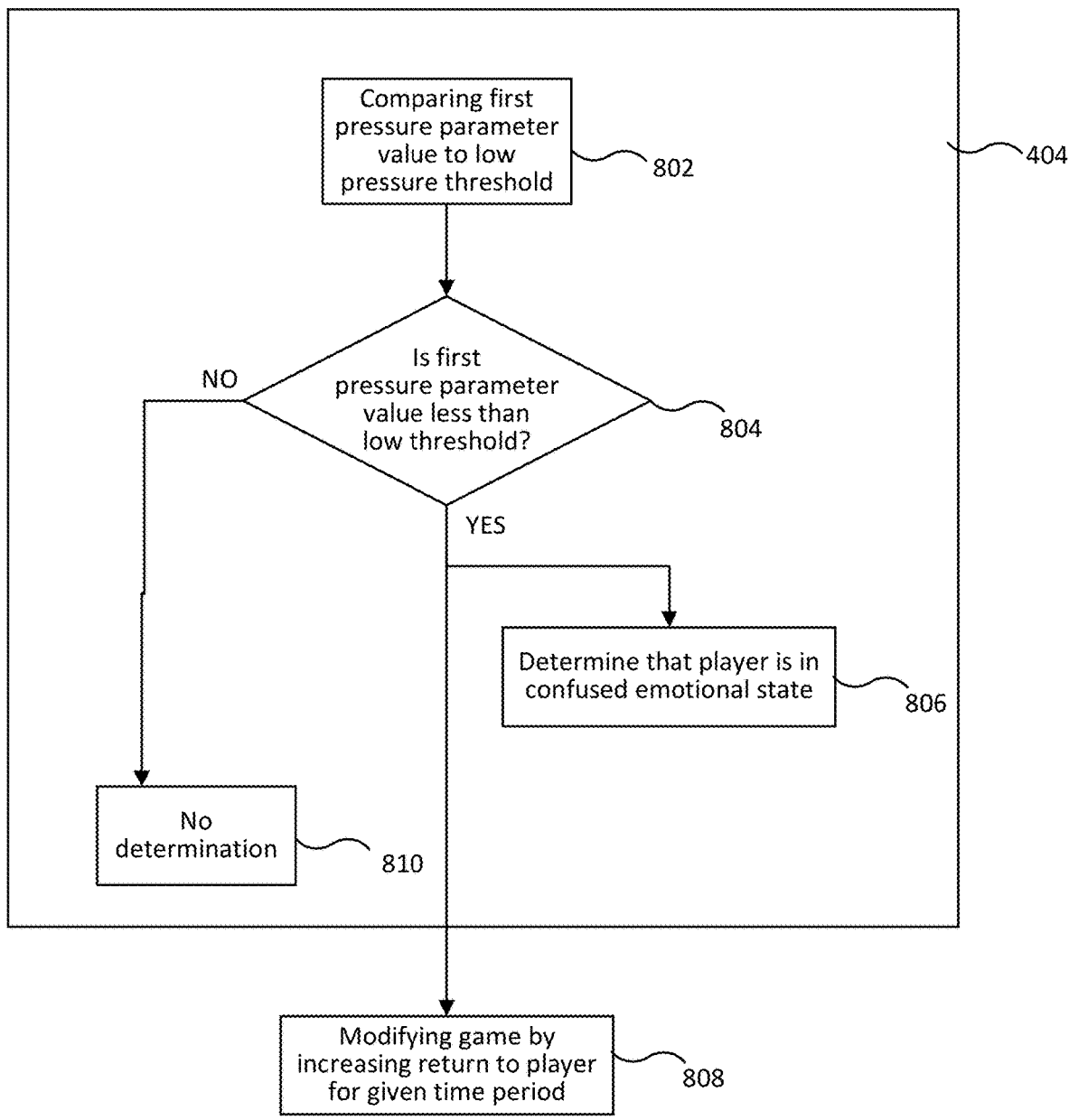
FIG. 8 is a flowchart illustrating operations of systems/methods according to some embodiments.

Reference is now made to FIG. 8, which is a flowchart illustrating operations of systems/methods according to some embodiments. According to some embodiments, determining the emotional state (404) includes comparing the first pressure parameter value to a low pressure parameter threshold (block 802). Operations may include determining, based on the comparison, whether the first pressure parameter value is less than the low pressure parameter threshold (block 804). If the first pressure parameter value is less than the low pressure parameter threshold, then it may be determined that the player is in a confused emotional state (block 806). In such cases, the game may be modified by increasing a return to player game play characteristic for a given time period to regain the interest of the player (block 808). Otherwise, if the first pressure parameter value is not less than the low pressure parameter threshold, the no determination may be made (block 810).

Figure 9:
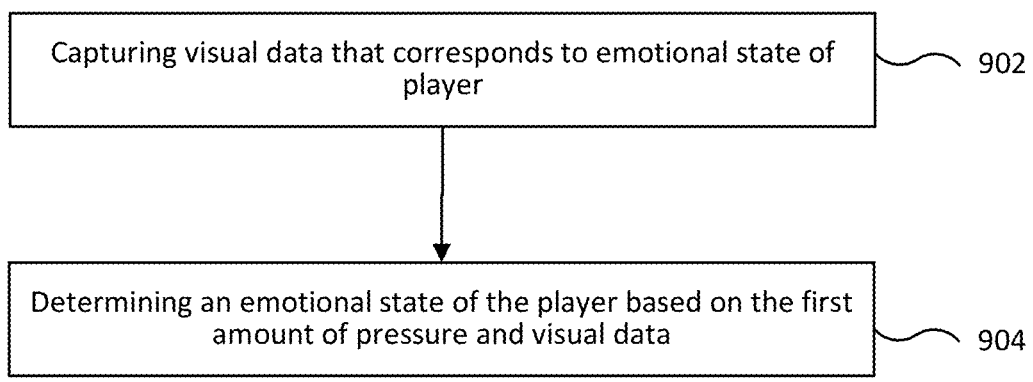
FIG. 9 is a flowchart illustrating operations of systems/methods according to some embodiments.

Reference is now made to FIG. 9, which is a flowchart illustrating operations of systems/methods according to some embodiments. Operations according to some embodiments include receiving, via an image capture device, visual data that corresponds to the emotional state of the player (block 902). In such embodiments, determining the emotional state of the player may be based on the amount of pressure being applied to the pressure sensitive input device 130 (block 904). Visual data may include any of facial recognition, thermal scanning, gesture inputs and/or posture detection and/or changes in any of these visually acquired properties.

Figure 10:
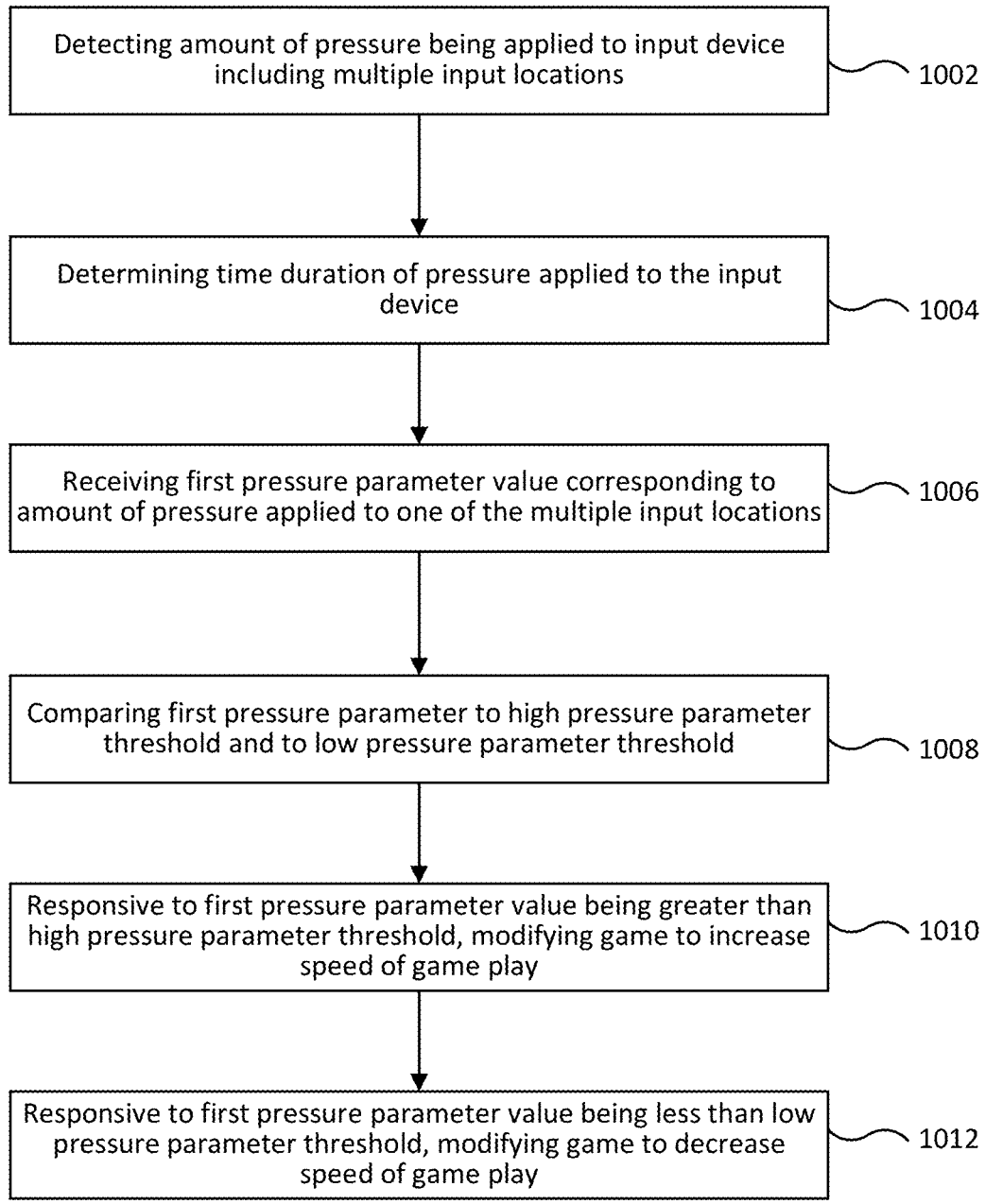
FIG. 10 is a flowchart illustrating operations of systems/methods according to some embodiments.

FIG. 10 is a flowchart illustrating operations of systems/methods according to some embodiments. Operations include detecting, by a pressure sensor of an input device of a gaming device, an amount of pressure applied by a player to the input device that includes multiple input locations (block 1002) and detecting, by the pressure sensor, a time duration of the pressure applied to the input device (block 1004). Operations further include receiving, into a processor circuit of the gaming device, a first pressure parameter value corresponding to the amount of pressure being applied to the input device at a first one of the locations (block 1006) and comparing the first pressure parameter value to a high pressure parameter threshold and to a low pressure parameter threshold that is lower than the high pressure parameter threshold (block 1008). Some embodiments include, responsive to the first pressure parameter value being greater than the high pressure parameter threshold, modifying the game play to increase a speed of game play (block 1010) and, responsive to the first pressure parameter value being less than the low pressure parameter threshold, modifying the game play to decrease a speed of game play (block 1012).

The user interface element(s) may be modified in many different ways, in response to different pressure and time combinations. For example, in response to the first pressure parameter value satisfying a predetermined pressure threshold, the user interface element may be modified to display a modified user interface element at a display device of the gaming device. Similarly, in response to the first pressure parameter value failing to satisfy the predetermined pressure threshold, the user interface element to may be modified to display another modified user interface element at the display device of the gaming device.

Alternatively, or in addition, the user interface element may be modified in response to the time value satisfying a predetermined time threshold, to display a modified user interface element at a display device of the gaming device, and/or, in response to the time value failing to satisfy the predetermined time threshold, to display different modified user interface elements at the display device. For example, in response to the first pressure parameter value satisfying a predetermined pressure threshold and the time value satisfying a predetermined time threshold, an audio device volume may be modified (i.e., increased or decreases) at a first predetermined rate, and in response to the first pressure parameter value failing to satisfy the predetermined pressure threshold and the time value satisfying the predetermined time threshold, the audio device volume may be modified at a second, lower, predetermined rate. In response to the first pressure parameter value satisfying the predetermined pressure threshold, the audio device volume may be modified by a particular volume amount if the time value fails to satisfy the predetermined time threshold, and may be modified by a lower volume amount lower than the first predetermined volume amount if the time value satisfies the predetermined time threshold.

In the above-description of various embodiments, various aspects may be illustrated and described herein in any of a number of patentable classes or contexts including any new and useful process, machine, manufacture, or composition of matter, or any new and useful improvement thereof. Accordingly, various embodiments described herein may be implemented entirely by hardware, entirely by software (including firmware, resident software, micro-code, etc.) or by combining software and hardware implementation that may all generally be referred to herein as a "circuit," "module," "component," or "system." Furthermore, various embodiments described herein may take the form of a computer program product comprising one or more computer readable media having computer readable program code embodied thereon.

Any combination of one or more computer readable media may be used. The computer readable media may be a computer readable signal medium or a non-transitory computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible non-transitory medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Various embodiments were described herein with reference to flowchart illustrations and/or block diagrams of methods, apparatus (systems), devices and computer program products according to various embodiments described herein. It will be understood that each block of the flowchart illustrations and/or block diagrams, and combinations of blocks in the flowchart illustrations and/or block diagrams, can be implemented by computer program instructions. These computer program instructions may be provided to a processing circuit of a general purpose computer, special purpose computer, or other programmable data processing apparatus to produce a machine, such that the instructions, which execute via the processing circuit of the computer or other programmable instruction execution apparatus, create a mechanism for implementing the functions/acts specified in the flowchart and/or block diagram block or blocks.

These computer program instructions may also be stored in a non-transitory computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be designated as "/". Like reference numbers signify like elements throughout the description of the figures.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall be construed to constitute a complete written description of all combinations and subcombinations of the embodiments described herein, and of the manner and process of making and using them, and shall support claims to any such combination or subcombination.

What is claimed is:

1. A gaming device comprising
an input device comprising:
   a plurality of input locations; and
   a pressure sensor to detect, for each input location, an amount of pressure applied by a player to the input device at the input location of the gaming device;
a processor circuit; and
a memory coupled to the processor circuit, the memory comprising machine-readable instructions that, when executed by the processor circuit, cause the processor circuit to:
   receive, from the pressure sensor, a first pressure parameter value corresponding to a first amount of pressure being applied by the player to the input device at a first input location for a first time interval comprising a first time duration;
   determine, based on the first amount of pressure, an emotional state of the player; and
   modify an operation of the gaming device based on the emotional state of the player.

2. The gaming device of claim 1, wherein instructions to determine the emotional state further cause the processor circuit to:
   determine a game performance trend that corresponds to player winning history data;
   compare the first pressure parameter value to a pressure parameter threshold; and
   responsive to the game performance trend indicating that the player has a winning history over a given previous time period and that the first pressure parameter value is greater than the pressure parameter threshold, determining that the emotional state of the player corresponding to a game is an excited positive emotional state.

3. The gaming device of claim 1, wherein instructions to determine the emotional state further cause the processor circuit to:
   determine a game performance trend that corresponds to player winning history data;
   compare the first pressure parameter value to a pressure parameter threshold; and
   responsive to the game performance trend indicating that the player has a losing history over a given previous time period and that the first pressure parameter value is greater than the pressure parameter threshold, determining that the emotional state of the player corresponding to the game is a negative emotional state.

4. The gaming device of claim 3, wherein responsive to determining that the emotional state of the player is a negative emotional state, modifying the operation of the gaming device comprises causing a winning event to occur corresponding to a game on the gaming device.

5. The gaming device of claim 1, wherein instructions to determine the emotional state further cause the processor circuit to determine the emotional state of the player based on the first time duration.

6. The gaming device of claim 1, wherein the first input location corresponds to a graphic of a user input element that receives inputs for the gaming device,
   wherein the instructions to receive the first pressure parameter value are further caused to receive a plurality of first pressure parameter values at the first input location in a given period of time,
   wherein the processing circuit is further caused to compare a quantity of the plurality of first pressure parameter values that are received during the given period of time to a threshold quantity of values corresponding to the given period of time, and
   based on the quantity of the plurality of first pressure parameter values being greater than the threshold quantity of values, determining that the emotional state of the player is negative.

7. The gaming device of claim 1, wherein the first input location corresponds to a graphic of a user input element that receives inputs for the gaming device,
   wherein, responsive receiving the first pressure parameter value for a given period of time causes a haptic response to be generated at the first input location of the gaming device.

8. The gaming device of claim 1, wherein the instructions to receive the first pressure parameter value are further caused to receive a plurality of first pressure parameter values,
   wherein the instructions to determine the emotional state of the player further cause the processor circuit to determine a speed of player inputs based on the plurality of first pressure parameter values, and
   wherein the instructions to modify the operation of the game further cause the processor circuit to adjust a speed of game play based on the speed of player inputs by delaying transitions of game graphic displays.

9. The gaming device of claim 1, wherein the processor circuit is further caused to:
   generate a plurality of baseline outcome game events that comprise expected reactions thereto; and
   store data corresponding to a plurality of first pressure parameter values that are received in response to ones of the plurality of baseline outcome game events as baseline pressure parameter values,
   wherein the instructions to determine the emotional state of the player further cause the processor circuit to determine a pressure difference between subsequently received first pressure parameter values to the baseline pressure parameter values, and
   wherein the instructions to modify the operation of the gaming device are performed responsive to the pressure difference exceeding a pressure difference threshold.

10. The gaming device of claim 9, further comprising updating the stored data corresponding to the plurality of first pressure parameter values based on subsequently presented baseline outcome game events.

11. The gaming device of claim 1, wherein the first input location comprises a portion of the plurality of input locations that correspond to a swiping input from the player,
    wherein the instructions to receive the first pressure parameter value further cause the processor circuit to receive a plurality of pressure parameter values at respective ones of the plurality of input locations, and
    wherein the instructions to determine the emotional state further cause the processor circuit to determine a characteristic of the swiping input based on the plurality of pressure parameter values.

12. The gaming device of claim 11, wherein the characteristic of the swiping input comprises a swiping stroke speed, and
    wherein instructions to determine the emotional state of the player are based on the plurality of pressure parameter values and the swiping stroke speed.

13. The gaming device of claim 11, wherein the instructions to determine the emotional state of the player are based on changes in a swiping stroke speed over a given time interval,
    wherein responsive to the swiping stroke speed increasing over the given time interval, the instructions to modify the operation of the gaming device cause the processor circuit to increase a speed of game play, and
    wherein responsive to the swiping stroke speed decreasing over the given time interval, the instructions to modify the operation of the gaming device cause the processor circuit to decrease the speed of game play.

14. The gaming device of claim 11, wherein the characteristic of the swiping input comprises a swiping stroke length,
    wherein the instructions to determine the emotional state of the player are based on changes in the swiping stroke length,
    wherein responsive to the swiping stroke length increasing over a given time interval, the instructions to modify the operation of the gaming device cause the processor circuit to decrease a speed of game play, and
    wherein responsive to the swiping stroke length decreasing over the given time interval, the instructions to modify the operation of the gaming device cause the processor circuit to increase the speed of game play.

15. The gaming device of claim 1, wherein instructions to determine the emotional state further cause the processor circuit to:
    compare the first pressure parameter value to a low pressure parameter threshold; and
    responsive to the first pressure parameter value being less than the low pressure parameter threshold, determining that the emotional state of the player is a confused emotional state.

16. The gaming device of claim 1, wherein instructions to determine the emotional state further cause the processor circuit to:
    compare the first pressure parameter value to a low pressure parameter threshold; and
    responsive to the first pressure parameter value being less than the low pressure parameter threshold, modifying game play by increasing a return to player value for a given time period.

17. The gaming device of claim 1, wherein further instructions cause the processor circuit to receive, via an image capture device, visual data that corresponds to the emotional state of the player, and
    wherein the instructions to determine the emotional state of the player further cause the processor circuit to receive the visual data and to determine the emotional state based on the visual data and the first amount of pressure.

18. A system comprising
    a processor circuit; and
    a memory coupled to the processor circuit, the memory comprising machine-readable instructions that, when executed by the processor circuit, cause the processor circuit to:
        receive, from a pressure sensor of an input device of a gaming device, a first pressure parameter value corresponding to a first amount of pressure being applied by a player to the input device at a first input location for a first time duration;
        determine, based on the first amount of pressure and the first time duration, an emotional state of the player; and
        modify an operating characteristic of the gaming device based on the emotional state of the player.

19. The system of claim 18, wherein responsive to the first amount of pressure exceeding a high pressure threshold, the instructions to modify the operating characteristic further cause the processor circuit to increase a speed of game play, and
    wherein responsive to the first amount of pressure being less than a low pressure threshold, the instructions to modify the operating characteristic further cause the processor circuit to decrease the speed of game play.

20. A method comprising:
    detecting, by a pressure sensor of an input device of a gaming device, an amount of pressure applied by a player to the input device that comprises a plurality of input locations;
    detecting, by the pressure sensor, a time duration of pressure applied to the input device;
    receiving, into a processor circuit of the gaming device, a first pressure parameter value corresponding to the amount of pressure being applied to the input device at a first one of the plurality of input locations;
    comparing the first pressure parameter value to a high pressure parameter threshold and to a low pressure parameter threshold that is lower than the high pressure parameter threshold;
    responsive to the first pressure parameter value being greater than the high pressure parameter threshold, modifying game play to increase a speed of game play; and
    responsive to the first pressure parameter value being less than the low pressure parameter threshold, modifying game play to decrease a speed of game play.

* * * * *